United States Patent [19]

Kortz et al.

[11] Patent Number: 5,216,688
[45] Date of Patent: Jun. 1, 1993

[54] SOLID STATE LASER WITH PUMPING LASER DIODES

[75] Inventors: Hans-Peter Kortz, Pansdorf; Walter Scrlac, Reinfield, both of Fed. Rep. of Germany

[73] Assignee: Adlas Gmbh & Co. KG, Lübeck, Fed. Rep. of Germany

[21] Appl. No.: 781,171
[22] PCT Filed: Apr. 30, 1990
[86] PCT No.: PCT/EP90/00693
  § 371 Date: Oct. 31, 1991
  § 102(e) Date: Oct. 31, 1991
[87] PCT Pub. No.: WO90/13930
  PCT Pub. Date: Nov. 15, 1990

[30] Foreign Application Priority Data

May 2, 1989 [DE] Fed. Rep. of Germany ....... 3914492

[51] Int. Cl.⁵ .............................................. H01S 3/094
[52] U.S. Cl. ......................................... 372/75; 372/36
[58] Field of Search ............................ 372/75, 36, 34

[56] References Cited

U.S. PATENT DOCUMENTS

| 3,538,455 | 11/1970 | Florio | 372/75 |
| 3,555,452 | 1/1971 | Nielsen et al. | 372/75 |
| 3,683,296 | 8/1972 | Scalise | 372/75 |
| 3,711,789 | 1/1973 | Dierschke | 372/75 |
| 3,771,031 | 11/1973 | Kay | 372/75 |
| 4,439,861 | 3/1984 | Bradford | 372/75 |
| 4,575,854 | 3/1986 | Martin | 372/75 |
| 4,719,631 | 1/1988 | Conaway | 372/34 |
| 4,756,002 | 7/1988 | Ruggieri et al. | 372/70 |

FOREIGN PATENT DOCUMENTS 2542652 7/1977 Fed. Rep. of Germany .

Primary Examiner—James W. Davie
Attorney, Agent, or Firm—Gottlieb, Rackman & Reisman

[57] ABSTRACT

A solid state type laser contains a laser rod (1) and at least one pumping module (2d, 2e) equipped with laser diodes (D) which is designed as a ring-shaped or partial ring-shaped module with a circumferential cooling duct (4). This geometry permits the lost heat of the laser diodes (D) to be effectively removed radially outward through the cooling duct (4), on the one hand, and through thermal conduction in the material of the module, on the other hand. The individual laser diodes are so arranged that the major axis of each rotationally non-symmetrical lobe of laser light, along which axis the main radiation power from the respective laser diode is obtained, lies in a plane substantially parallel to the longitudinal axis of the laser rod.

7 Claims, 1 Drawing Sheet

SOLID STATE LASER WITH PUMPING LASER DIODES

The present invention relates to a solid state laser of the type having a laser rod and a pumped light source in the form of a pumping module constituted by a plurality of laser diodes arranged in at least one row.

BACKGROUND OF THE INVENTION

The use of laser diodes to form a pumped light source for a solid state laser has been known for some time. The laser diodes are disposed on a module in a straight row, the module being disposed parallel to the longitudinal axis of the cylindrical laser rod spaced a small distance form the laser beam (IEEE Journal of Quantum Electronics, Vol 24, No. 6, June 1988, pages 895 to 911).

The use of laser diodes as a pumped light source is advantageous due to the relatively high power of the laser light (compared with light-emitting diodes), but it simultaneously raises certain problems with respect to the cooling.

A special feature of pumping laser diodes is that the radiated lobe of light is not rotationally symmetrical. The angle of dispersion parallel to the mounting surface is considerably smaller than perpendicular thereto. The beam does not diverge as quickly in the direction parallel to the mounting surface. Perpendicular to the mounting surface the angle of dispersion is very great. In the abovementioned known assembly this means that (unless an optical system is used) part of the light energy fails to be coupled into the laser rod and is thus lost.

It is known (U.S. Pat. No. 4,719,631) to cool pumping laser diode arrays by arranging a plurality of diodes of a pumping array disposed parallel to the longitudinal axis of the laser rod individually on respective ceramic cooling wafers, several such arrays being distributed about the laser rod. The aligned laser diodes thus form an array likewise extending in the longitudinal direction of the laser rod. The cooling measures are rather elaborate and expensive. The mechanical structure of such a solid state laser is extremely elaborate and expensive.

There is known from German published patent application No. DE-A 2,542,652 a solid state laser wherein the solid state medium is a hollow cylinder internally of which there is provided a rod-shaped diode array and externally of which it is surrounded by an additional tube-shaped diode array. By means of this arrangement there are defined between the solid state medium and the two diode arrays two annular hollow spaces for a cooling fluid. The diodes in both arrays are constructed as individual diodes, but as an alternative it is nonetheless possible to use fully integrated diode arrays in which the diodes can also be laser diodes. The indicated possible cooling by filling the annular spaces with a suitable cooling fluid makes it necessary to provide special sealing means, and over and above that the cooling fluid must have an appropriate refractive index.

BRIEF DESCRIPTION OF THE INVENTION

The invention is based on the problem of providing a solid state laser of the aforesaid type wherein a relatively large light quantity passes from the pumping laser diodes into the laser rod and which permits high-power operation due to the possibility of efficient cooling.

According to the invention, to achieve the solution to the stated problem, a pumping module bearing a circular or arcuate array of laser diodes is designed as a ring or partial ring, the module is disposed, not parallel to the longitudinal axis of the laser rod as in the prior art, but in a plane perpendicular to the longitudinal axis of the laser rod, and the individual laser diodes are so arranged that the major axis of each radiated lobe of laser light, along which axis the main radiation power is obtained, lies in a plane substantially parallel to the longitudinal axis of the laser rod. Since the angle of dispersion of the laser diodes is greater perpendicular to their mounting surface than the angle of dispersion parallel to the mounting surface, i.e., parallel to the axis of the laser rod, a large light quantity can pass into the laser rod without using any optical system, even if the distance is relatively great between the pumping module and the laser rod.

The pumping modules according to the present invention can have an almost semicircular design, for example. They can be disposed in a stack in the longitudinal direction of the laser rod and/or they can be offset form the laser rod at an angle, whereby each module is always oriented in a plane extending perpendicular to the longitudinal axis of the laser rod.

The laser diodes are preferably disposed in the inner edge area of the pumping module. This provides sufficient room for dissipation of the power loss in the back area, i.e. in the radially outside area, of the pumping module.

The invention preferably provides for at least one cooling duct for a coolant (water or gas) in the pumping module, this cooling duct being formed as a circumferential channel on the radial outside with respect to the array of laser diodes.

Such a cooling duct can be produced in a particularly simple way by milling an annular groove out of the massive material (e.g. copper) of the pumping module bottom and mounting a cover plate on the bottom of the pumping module to form the bottom of the annular groove. Supply and removal lines can be readily connected to the ring channel.

BRIEF DESCRIPTION OF THE DRAWINGS

In the following, embodiment examples of the invention shall be explained in more detail with reference to the drawing, in which.

DETAILED DESCRIPTION OF THE INVENTION

Figure 1:
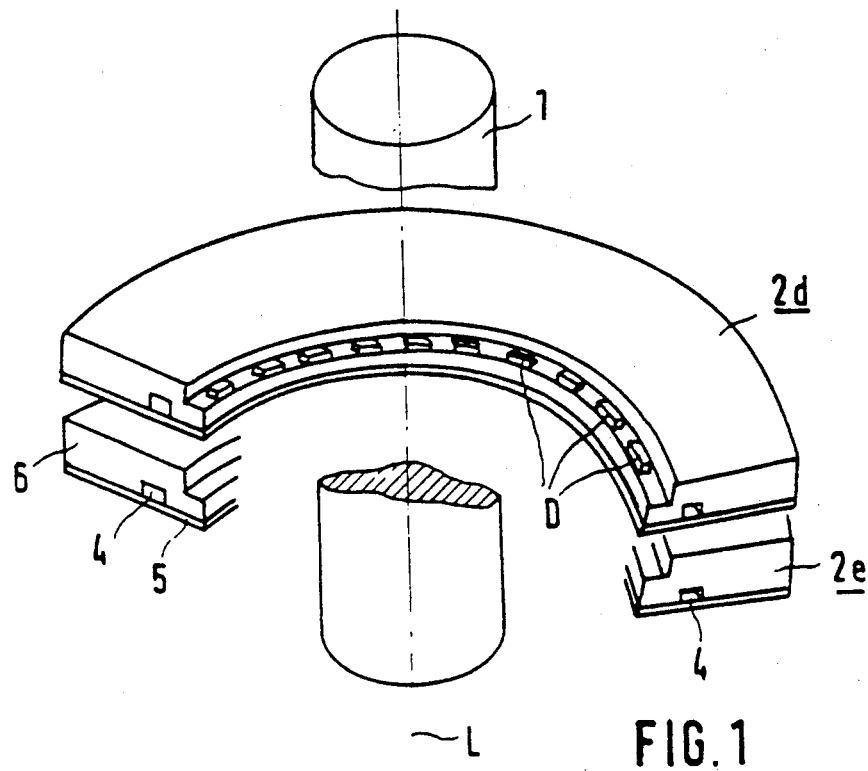
FIG. 1 shows a schematized perspective partial view of one embodiment of a solid state laser according to the present invention.

According to FIG. 1, a solid state laser contains a laser rod 1 made of a customary laser crystal. In various parallel planes extending perpendicular to longitudinal axis L of laser rod 1 there are pumping modules 2d and 2e and optionally further such pumping modules not shown in the drawing.

Figure 2:
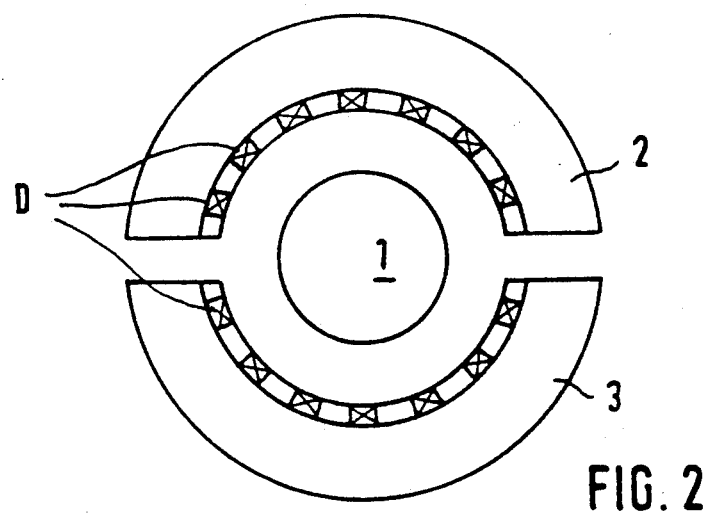
FIG. 2 shows a top view of another embodiment of a solid state laser according to the invention.

FIG. 2 shows a top view of an assembly of a solid state laser wherein a laser rod 1 is almost completely surrounded by two pumping modules 2 and 3 offset at an angle. These pumping modules 2 and 3 can also be stacked perpendicular to the pane of projection, i.e., in the manner of the modules 2d and 2e shown in FIG. 1.

The pumping modules are all of identical design. Each module consists of a massive block of material, e.g. a copper block, having formed in its inner edge area a step on which a row of laser diodes D are disposed. The connections of the laser diodes are not shown in the drawing.

Each pumping module comprises a massive partial ring 6 and a bottom portion 5. In the bottom of partial ring 6 a circumferential groove 4 is milled to form a cooling duct for a coolant, e.g. water, after bottom plate 5 is mounted. The coolant is guided through circumferential groove or partially circumferential groove 4 via connections not shown here.

As a modification of the embodiments described above, radial grooves can also be provided for the coolant.

The invention also includes, as a special aspect, a linear assembly of modules whose special feature is that an uninterrupted cooling duct is formed in the vicinity of the laser diodes.

The ring-shaped assembly of laser diodes D shown in FIGS. 1 and 2 leaves a lot of room in the outer area of the pumping modules for radiation of lost heat which promotes the cooling of the pumping module. The relatively close assembly of laser diodes D permits a large light quantity to pass into laser rod 1.

The radiated lobe or spot of laser light provided by each individual diode D is not rotationally symmetrical, i.e., it is not circular but rather has the form of an ellipse having a major axis and a minor axis, with the main radiation power from each laser diode being obtained along the major axis of the respective lobe of laser light. In accordance with the present invention, the major axis of each lobe of laser light is disposed in a plane that extends substantially parallel to longitudinal axis L of laser rod 1. Therefore, maximum power and virtually all the laser light passes form the diodes into laser rod 1.

We claim:

1. A solid state laser including a laser rod having a longitudinal axis, and a light source formed as a pumping module and comprising a plurality of laser diodes disposed in at least one row adjacent said laser rod and arranged to emit respective radiated rotationally nonsymmetrical lobes of laser light each of which has a major axis and a minor axis, with the main radiation power form each laser diode being obtained along said major axis of the respective lobe of laser light; wherein the improvement comprises:

at least one ring-shaped or partial ring-shaped body constituting a base portion of said pumping module, said body being disposed in a plane extending perpendicular to said longitudinal axis of said laser rod and supporting said laser diodes in a correspondingly curved row, and the individual laser diodes being arranged such that said major axis of each lobe of laser light is disposed in a plane substantially parallel to said longitudinal axis or said laser rod.

2. The solid state laser of claim 1, wherein the improvement further comprises that a plurality of pumping modules are provided, each having a body constituting a base portion of that module, and said bodies being arranged in a stack-like array disposed parallel to said longitudinal axis of said laser rod.

3. The solid state laser of claim 1 or 2, wherein the improvement further comprises that a plurality of partial ring-shaped pumping modules are offset at an angle beside said laser rod.

4. The solid state laser of claim 1 or 2, wherein the improvement further comprises that at least one cooling duct for a coolant (e.g. water or gas) is formed in said body of each pumping module.

5. The solid state laser of claim 4, wherein the improvement further comprises that said cooling duct in said body of each pumping module is formed as a circumferential channel on the radial outside with respect to said row of laser diodes.

6. The solid state laser of claim 4, wherein said improvement further comprises that the cooling duct is formed in the vicinity of said row of laser diodes.

7. The solid state laser of claim 4, wherein the improvement further comprises that said body of each pumping module has a massive section of copper or like thermally conductive material, that said cooling duct of said body of each pumping module is formed as an arcuate downwardly open groove in the bottom of said massive section of the respective body of that pumping module, and that a cover plate lies against said bottom of said body of each pumping module and in overlying relation to the respective groove.

* * * * *